United States Patent [19]

Coleman

[11] Patent Number: 5,003,267
[45] Date of Patent: Mar. 26, 1991

[54] MEASURING ELECTRICAL IMPEDANCE OF LOW CONDUCTIVITY SAMPLES TO MONITOR MICROBIAL GROWTH

[75] Inventor: Barrie B. Coleman, Salisburh, Great Britain

[73] Assignee: Public Health Laboratory Health Service Board, England

[21] Appl. No.: 435,372

[22] PCT Filed: Mar. 8, 1989

[86] PCT No.: PCT/GB89/00230
§ 371 Date: Dec. 22, 1989
§ 102(e) Date: Dec. 22, 1989

[87] PCT Pub. No.: WO89/08838
PCT Pub. Date: Sep. 21, 1989

[30] Foreign Application Priority Data

Mar. 8, 1988 [GB] United Kingdom ............ 8805488

[51] Int. Cl.$^5$ ............................................ G01N 27/02
[52] U.S. Cl. .................................. 324/442; 324/445; 324/450
[58] Field of Search ............... 324/442, 445, 450, 439

[56] References Cited

U.S. PATENT DOCUMENTS

| | | | |
|---|---|---|---|
| 3,417,329 | 12/1968 | Landis et al. | 324/445 |
| 3,735,247 | 5/1973 | Harker | 324/445 |
| 4,376,026 | 3/1983 | Hoffman et al. | 324/442 |
| 4,876,504 | 10/1989 | Blake et al. | 324/445 |

FOREIGN PATENT DOCUMENTS

| | | | |
|---|---|---|---|
| 0593163 | 2/1978 | U.S.S.R. | 324/442 |
| 0879429 | 11/1981 | U.S.S.R. | 324/442 |

*Primary Examiner*—Reinhard J. Eisenzopf
*Assistant Examiner*—Maura K. Regan
*Attorney, Agent, or Firm*—Kirschstein, Ottinger, Israel & Schiffmiller

[57] ABSTRACT

Apparatus for measuring the electrical impedance of low conductivity samples, and particularly microbial suspensions, has a coil surrounding a tubular sample container. A capacitive pick-up on the sample wall provides an input to a variable gain amplifier driving the coil. The resident frequency of the circuit is measured to provide an indication of sample conductivity.

11 Claims, 3 Drawing Sheets

MEASURING ELECTRICAL IMPEDANCE OF LOW CONDUCTIVITY SAMPLES TO MONITOR MICROBIAL GROWTH

BACKGROUND OF THE INVENTION

1. Field of the Invention

This invention relates to apparatus for measuring the impedance of a low conductivity sample. In an important example, the apparatus can be used to monitor low level microbial growth where it is typically necessary to measure electrical conductivities in the range 0.001 to 30 mS/cm$^{-1}$.

2. Description of Related Art

It is well established that measurement of the electrical impedance of bacteria suspended in a growth medium can provide useful information concerning bacterial growth. This has been done in some cases by inserting electrodes in the sample and making a direct impedance measurement. Advantages have been seen, however, in employing non-invasive methods and a number of oscillometric techniques have been suggested which can readily be operated in a non-invasive manner, that is to say with no physical contact between the sample and any electrode of the measuring system. In these oscillometric techniques, a sample of the medium is disposed in relation to an electrical resonant circuit in such a manner that the frequency of reasonance is indicative of the sample impedance.

The known techniques often fall into two categories: inductive techniques where the sample is placed within a measurement coil, and capacitive techniques in which the test sample is placed between electrodes to form a capacitor. Inductive oscillometers perform best with highly condcutive samples and are therefore used only rarely in this and related apllications. A number of different arangements of capacitive oscillometers have been proposed but difficulties have been found with existing arrangements, particularly in their resolution. It is believed that for microbial suspension studies, a resolution is desirable of 1 in $10^{-8}$ or better.

SUMMARY OF THE INVENTION

It is an object of this invention to provide an improved apparatus for measuring the electrical impedance of a low conductivity sample and in particular to provide apparatus having high resolution.

Accordingly, the present invention consists in apparatus for measuring the electrical impedance of a low conductivity sample, comprising a sample container having an electrically insulating wall; coil means positioned adjacent the container; electrode means provided on the external wall surface; feedback means serving to apply to the coil means a current related to the voltage sensed by the electrode means; and monitoring means for deriving an output indicative of the electrical impedance of the sample.

Advantageously, said monitoring means serves to determine the natural frequency of oscillation.

Preferably, electrical screening means are provided between said coil means and said electrode means.

In an important form of the invention, there is provided variable gain amplifier means between said electrode means and said coil means, the gain of said amplifier means being adapted to reduce with increasing frequency.

Advantageously, the gain of said amplifier is adapted to reduce with increasing amplitude of sensed voltage.

BRIEF DESCRIPTION OF THE DRAWINGS

The invention will now be described by way of example with reference to the accompanying drawings in which.

DETAILED DESCRIPTION OF THE PREFERRED EMBODIMENTS

Figure 1:
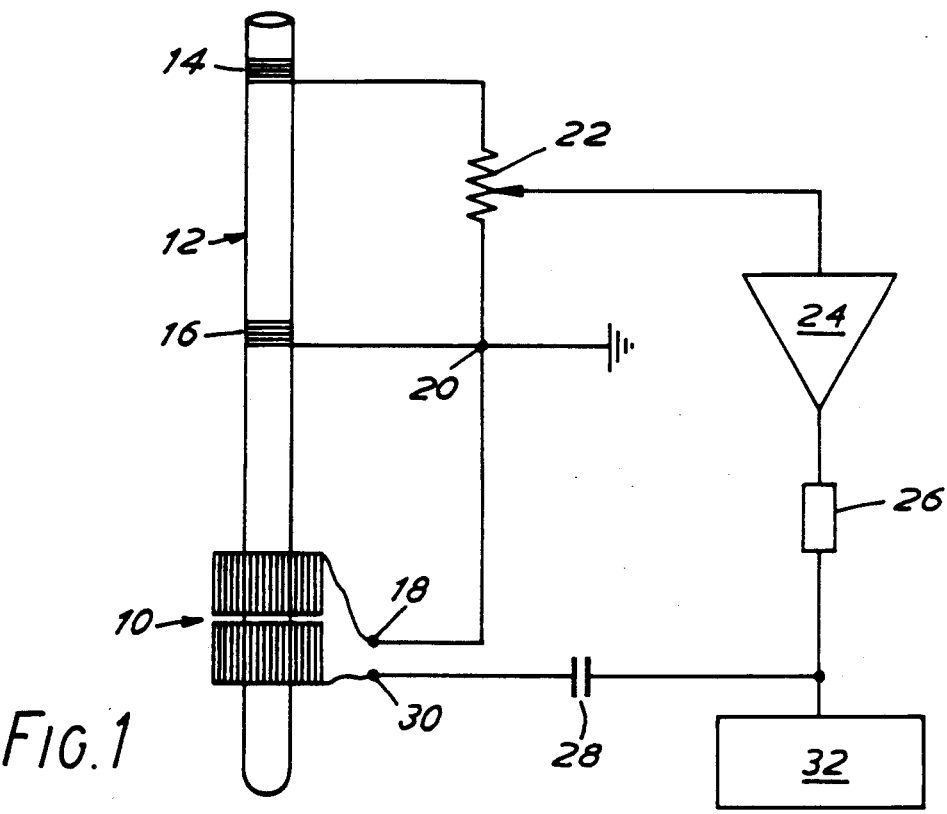
FIG. 1 is a somewhat diagrammatic view of apparatus according to this invention.

Referring to FIG. 1, a double toroid coil 10 is disposed about one end of an electricallly insulating sample tube 12. Each toroid comprises a single winding of 0.25mm insulated copper upon a ferrite core. The sample tube is formed of glass having in this example an internal diameter of 4.5mm and an external diameter of 5.0mm. Towards the opposite end of this sample tube, there is provided a capacitive pick-up 14 engaging the outer wall of the sample tube. This comprises a number of turns of bare wire embedded in silver loaded epoxy resin to form a conductive sleeve. A similarly formed shield electrode 16 is positioned midway between the coil pick-up 10 and the pick-up 14, with the distance between the coil and the pick-up being around 5cm.

One terminal 18 of the coil 10 is connected with an earth terminal 20, as is also the shield electrode 16. A potentiometer 22 is connected between the pick-up 14 and the earth terminal 20, with the wiper connected as the input to an amplifier 24. Though shown schematically in the drawing, amplifier 24 is a three stage amplifier having tailored gain characteristics as described more fully hereafter. The output of amplifier 24 is connected through resistance 26 and capacitance 28 with the second terminal 30 of the double coil. The junction of resistance 26 and capacitance 28 is taken to frequency meter 32.

Figure 2:
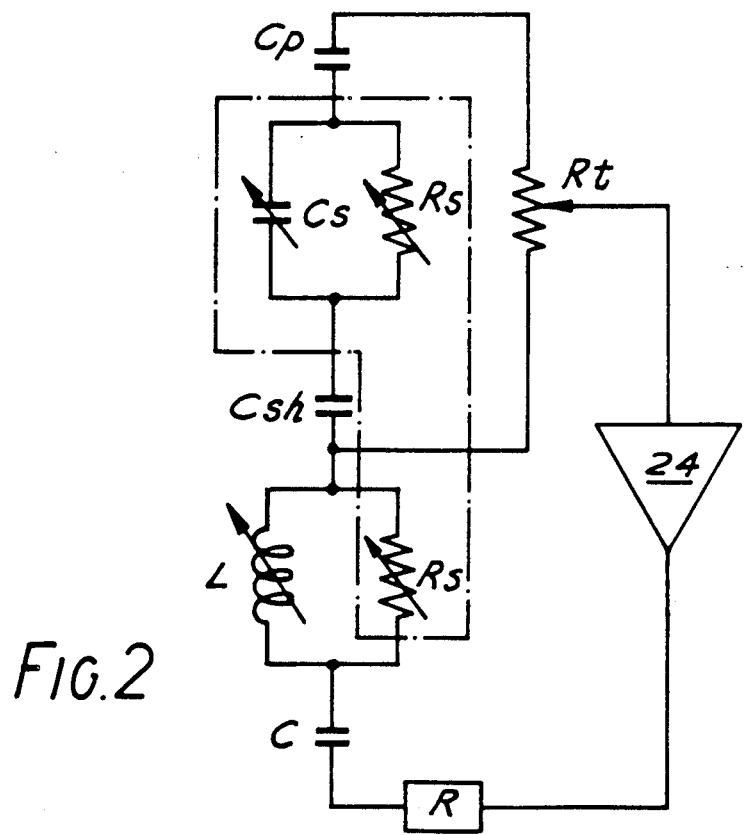
FIG. 2 is an electrical circuit diagram of the apparatus shown in FIG. 1, including an equivalent circuit for the sample.

Referring now to FIG. 2, there is shown an electrical circuit diagram in which the sample cell is modelled as variable resistance $R_s$ and variable capacitance $C_s$. The resistance of potentiometer 22 is represented by $R_t$ and the capacitances associated with pick-up 14 and shield 16 are represented by $C_p$ and $C_{sh}$ respectively. The inductance of doubt coil 10 is represented by L. The model of the sample cell provides resistances $R_s$ in parallel respectively with inductance L and with sample capacitance $C_s$.

Figure 3:
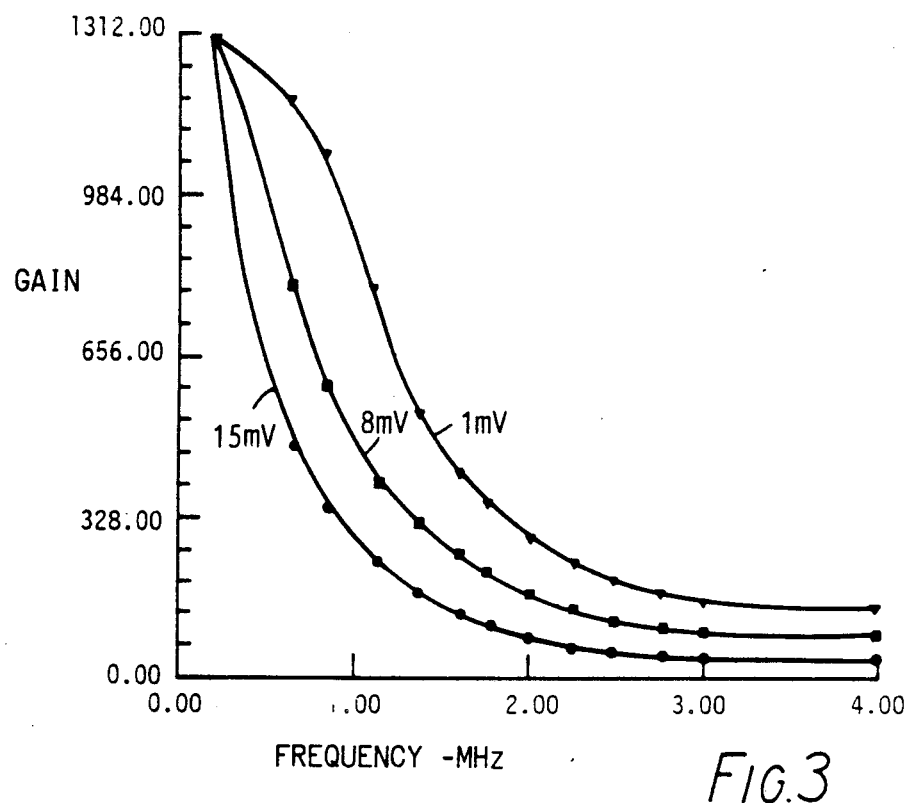
FIG. 3 is a graph illustrating the gain characteristics of an amplifier forming part of the circuit shown in FIG. 1.

The amplifier chain is provided with internal, frequency dependent, negative feedback producing a substantial roll-off in gain above 600 KHz. The variation in gain with frequency is shown in FIG. 3 for three input signal levels. It will be noticed that the amplifier is additionally designed to produce a reduction in gain with increasing input levels. Over the signal amplitudes and frequencies of interest, there is a reduction in gain per millivolt increase in signal input level of from 1% to 10%, preferably 2% to 5% and in this example approximately 3. Over the frequency range 600 KHz to 3.9 MHz, the output impedance of the amplifier varies from 0.02 K Ohm to 16.5 K Ohm.

The manner of operation of the described device is believed to be as follows.

The effect of a noise generated alternating current in the coil means 10 is to produce a time varying magnetic field in the sample creating an emf inducing an alternating charge displacement within the sample. The phenomenon of polarisation in a pure dielectric is well understood and it is believed that low conductivity sample can be views as "degraded dielectrics" with a disturbing electric field then producing charge displacement of both free charges and polarisable groups. It is these charge displacements that are sensed electrostatically by the capacitive pick-up 14.

For a given amplifier, sufficient signal must of course be available at low conductivities to excite oscillation. This means the inductive field must high enough at low conductivities to generate a threshold signal. High frequencies produce low field penetration into the sample because of skin effects so that the initial frequency should be low to initial oscillation and must remain at such a level that there is field penetration beyond the sample tube wall and into a sufficient depth of the sample.

Figure 4:
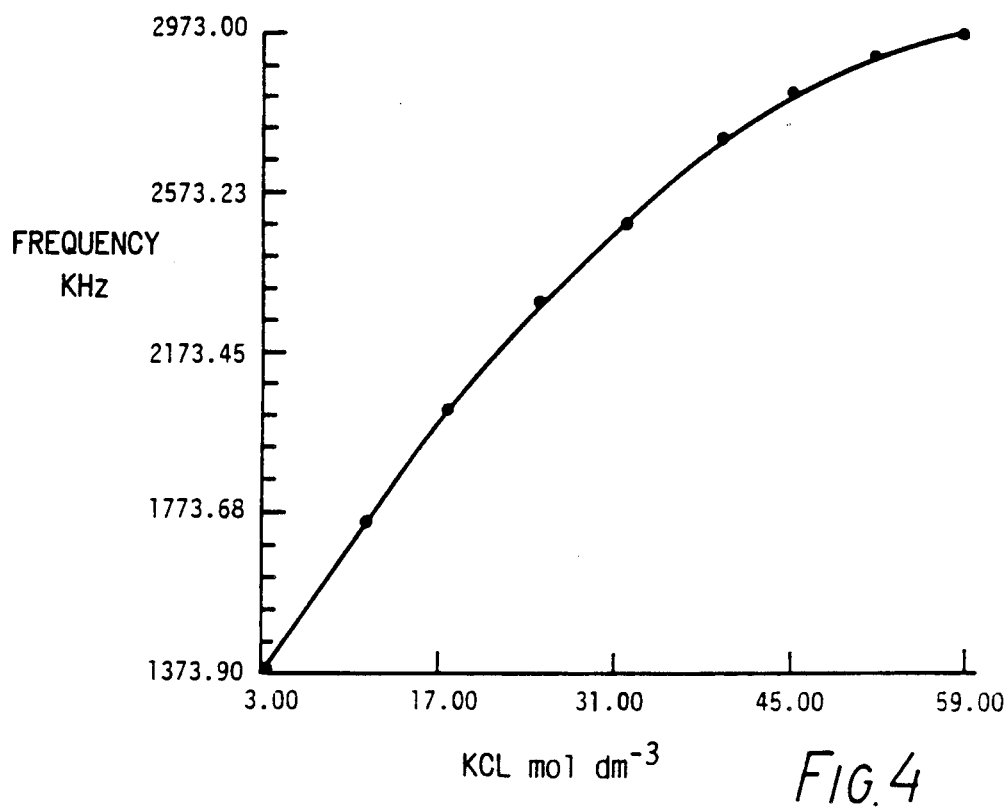
FIG. 4 is a calibration curve for the apparatus of FIG. 1.

The LC drive circuit to the sample results in a "off-resonance" effect as the sample conductivity changes with a simultaneous increase in signal amplitude as the feed (via the sample itself) increases with increasing conductivity. The amplifier 24 does not become saturated because of the increase in output impedance which begins at around 600 KHz. The frequency of oscillation of the system is found to be a reproducible indication of sample conductivity. The apparatus can be calibrated with solutions of known conductivity such as different concentrations of KCl. A graph of such a calibration is shown in FIG. 4 with the variation in concentration of KCl amounting to a shift in conductivity of approximately 5.4 mS/cm$^{-1}$.

The described arrangement is found to have high resolution and provides in the typical circuit arrangement a resolution in terms of frequency shift per unit change in conductivity of around 300 Hz per $10^{-3}$mS/cm$^{-1}$. It is believed that the high resolution results in part from the face that, as compared with known inductive oscillometers, the sample not only varies the self inductance of the measuring coil but also forms part of the feedback path in the resonant circuit. The sample does not simply vary the value of the inductance, but forms a series of LC and RC active filters by changing the output impedance of the amplifier as a function of signal amplitude in the feedback path.

Figure 5:
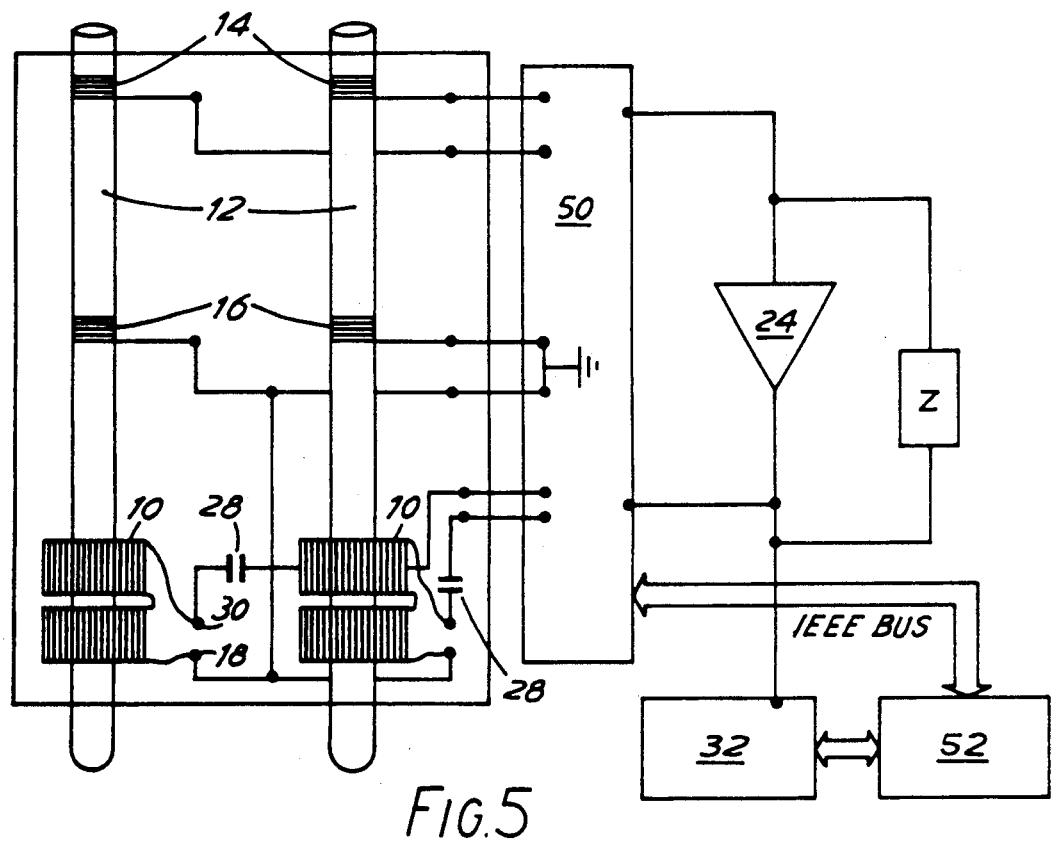
FIG. 5 is a diagram similar to FIG. 1, illustrating a modification.

The comparatively large frequency shift in practical applications (a shift of 200 mS to 400 mS in microbial impediometry leading to a frequency change of typically 56 KHz to 112 KHz) provides excellent resolution. Moreover, the resolution is found to be constant within acceptable limits over conduction ranges typical of microbial suspensions, enzyme reactions and electrolytes in reagent concentrations. The fact that the measurement is frequency based, affords the expected advantages in precision and avoidance of interference. Because the operting frequencies are relatively low, it is possible to employ multiplexing techniques with arrays of sample containers. Referring to FIG. 5, two sample containers are shown, though a considerably larger number could be included. So far as is appropriate, the same reference numerals are employed as in FIG. 1. Between the amplifier 24 and the sample pick-ups and coils, there is disposed a switching network 50 driven by a controller 52. This may be a commerically available PC such as Hewlett Packard 86. The frequency meter, which may conveniently be the commercially available model Schlumberger 2720, is additional connected with the controller 50. The controller is adapted to provide an output in any convenient form.

Figure 6:
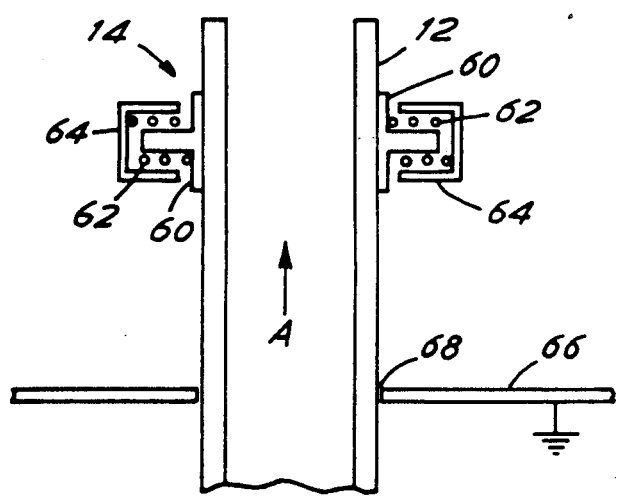
FIG. 6 is a part view of apparatus according to this invention illustrating a further modification.

A further modification is illustrated in FIG. 6. The capacitive pick-up shown generally at 14 comprises two electrodes 60 each biassed into contact wit the tube wall through a compression spring 62 acting against a housing 64. The shield electrode takes the form of a grounded plate 66 having an aperture 68 within which the sample tube 12 is a close fit. In this arrangement, the sample tube 12 can be slidably withdrawn from the apparatus in the direction of arrow A. It therefore becomes possible to use disposable, pre-filled and sterilised sample tubes with obvious advantages in terms of containment and transport of potentially hazardous samples.

It will be understood that this invention has been described by way of examples only and variety of modifications are possible without departing from the scope of the invention. Thus, for example, still further alternatives are available for the capacitive pick-up, and whilst a toroidal coil is preferred, alternative coil means exist. It will be further be clear to the skilled man that the geometry as exemplified by the diagrams of FIG. 1, can be varied widely.

I claim:

1. Apparatus for measuring the electrical impedance of a low conductivity sample, comprising a sample container having an electrically insulating wall; coil means positioned adjacent the container; electrode means provided on the external wall surface; feedback means serving to apply to the coil means a current related to the voltage sensed by the electrode means thereby to excite oscillation at a natural frequency of oscillation; and monitoring means for determining said natural frequency of oscillation and deriving therefrom an output indicative of the electrical impedance of the sample.

2. Apparatus according to claim 1, wherein the sample container is elongate and said coil means and said electrode means are spaced along the length of the container.

3. Apparatus according to claim 2, wherein said coil means comprises at least one toroidal coil having an axis aligned with the length of the sample container.

4. Apparatus according to claim 1, wherein said coil means comprises at least one toroidal coil.

5. Apparatus according to claim 1, wherein said feedback means comprises variable gain amplifier means positioned between said electrode means and said coil means, the gain of said amplifier means being adapted to reduce within increasing frequency.

6. Apparatus acccording to claim 5, wherein the gain of said amplified means reduce by 5 to 20 dB and preferably approximately 9 dB from frequencies of 500 KHz to 4 MHz.

7. Apparatus according to claim 1, wherein said feedback means comprises variable gain amplifier means, the gain of said amplifier means being adapted to reduce with increasing voltage levels sensed by the electrode means.

8. Apparatus according to claim 7, wherein said gain reduces by from 2% to 5% preferably approximately 3% per millivolt increase in sensed voltage.

9. Apparatus according to claim 1, wherein the sample container is slidably removable from said coil means and said electrode means.

10. Apparatus according to claim 9, wherein said electrode means comprises an electrode resiliently biassed into contact with the external wall surface of the container.

11. Apparatus according to claim 1, wherein electrical screening means are provided between said coil means and said electrode means.

* * * * *